US010561506B2

(12) United States Patent
Boiten et al.

(10) Patent No.: US 10,561,506 B2
(45) Date of Patent: Feb. 18, 2020

(54) ORTHOPEDIC JOINT SYSTEM

(71) Applicant: OTTO BOCK HEALTHCARE GMBH, Duderstadt (DE)

(72) Inventors: Herman Boiten, Gottingen (DE); Clemens Kimmig, Oppenau (DE); Elmar Dittrich, Gottingen (DE)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 0 days.

(21) Appl. No.: 15/324,916

(22) PCT Filed: Jul. 9, 2015

(86) PCT No.: PCT/EP2015/065684
§ 371 (c)(1),
(2) Date: Jan. 9, 2017

(87) PCT Pub. No.: WO2016/005491
PCT Pub. Date: Jan. 14, 2016

(65) Prior Publication Data
US 2017/0202686 A1 Jul. 20, 2017

(30) Foreign Application Priority Data
Jul. 11, 2014 (DE) .................. 10 2014 010 254

(51) Int. Cl.
A61F 2/64 (2006.01)
A61F 2/68 (2006.01)

(52) U.S. Cl.
CPC .......... *A61F 2/64* (2013.01); *A61F 2002/6854* (2013.01)

(58) Field of Classification Search
CPC .. A61F 2/60; A61F 2/601; A61F 2/604; A61F 2/605; A61F 2/64; A61F 2/642;
(Continued)

(56) References Cited

U.S. PATENT DOCUMENTS 3,739,404 A * 6/1973 Gelbenegger ............ A61F 2/64
602/16
4,034,419 A 7/1977 Roberts
(Continued)

FOREIGN PATENT DOCUMENTS

DE 2848305 A1 5/1979
DE 8515598 U1 7/1985
(Continued)

OTHER PUBLICATIONS

PCT International Search Report for PCT International Patent Application No. PCT/EP2015/065684, dated Dec. 15, 2015.

*Primary Examiner* — Christie L Bahena
(74) *Attorney, Agent, or Firm* — Holland & Hart, LLP

(57) ABSTRACT

An orthopedic joint system having an upper part and a lower part mounted thereon so as to pivot about a pivoting axis, and a pawl which prevents in a locking position any relative movement between the upper part and the lower part about the pivoting axis, and allows in a release position a relative movement about the pivoting axis. The pawl, in the locking position, interlockingly engages a locking element and can be shifted to the release position via a pull element, a first end of the pull element being attached to the upper part or to the lower part and moved along the outside of the pawl in a curved section, and a second end of the pull element being provided with an actuating device which causes the curved section to be shortened and the pawl to be moved to the release position when the actuating device is actuated.

20 Claims, 5 Drawing Sheets

(58) Field of Classification Search
CPC ................ A61F 2/644; A61F 2002/607; A61F 2002/608; A61F 2002/648; A61F 2002/6854; A61F 2005/0158; A61F 2005/016; A61F 2005/0162
See application file for complete search history.

(56) References Cited

U.S. PATENT DOCUMENTS

| | | | |
|---|---|---|---|
| 4,232,405 A | | 11/1980 | Janovsky |
| 4,685,926 A | | 8/1987 | Haupt |
| 5,545,233 A | | 8/1996 | Fitzlaff |
| 5,571,210 A | * | 11/1996 | Lindh .................. A61F 2/66 623/38 |
| 5,888,237 A | | 3/1999 | Shiraishi et al. |
| 2007/0083272 A1 | | 4/2007 | Van De Veen et al. |
| 2007/0208431 A1 | | 9/2007 | Risinger et al. |
| 2010/0191347 A1 | * | 7/2010 | Pusch .................. A61F 2/60 623/27 |

FOREIGN PATENT DOCUMENTS

| | | | | |
|---|---|---|---|---|
| DE | 4233247 A1 | | 4/1994 | |
| DE | 20305231 | * | 4/2003 | ............ F15B 15/14 |
| DE | 202004008014 U1 | | 10/2004 | |
| DE | 10351916 A1 | | 6/2005 | |
| DE | 202008002764 U1 | | 8/2008 | |
| DE | 102012009653 A1 | | 11/2013 | |
| EP | 2664304 A2 | | 11/2013 | |
| GB | 2194443 A | | 3/1988 | |
| WO | WO0074610 | * | 6/1999 | |
| WO | 0074610 A1 | | 12/2000 | |

\* cited by examiner

ORTHOPEDIC JOINT SYSTEM

TECHNICAL FIELD

The invention relates to an orthopedic joint system having an upper part and a lower part, which is mounted on the upper part such that it can be pivoted about a pivot axis, and a catch, which, in a locked position, locks movement of the upper part relative to the lower part about the pivot axis and, in a release position, allows relative movement about the pivot axis, wherein, in the locked position, the catch engages in a form-fitting manner in a locking element and can be shifted into a release position via a pulling element.

BACKGROUND

Orthopedic joint systems may be designed, in particular, in the form of so-called lockable knee joints, which can usually be locked in the maximally extended position, in order to ensure that the patient enjoys a high level of stability while standing. Lockable knee joints are used usually for low-mobility patients for whom the focus is to ensure maximum stance stability and to allow a sitting-down action and sitting with a leg bent. For sitting down, the locking means is released, and therefore the patient can sit down with his foot placed on the floor. The sitting-down movement can be braked via a straightforward damper device. A prosthetic knee joint with a locking means and a hydraulic damping means for sitting down is described, for example, in DE 103 51 916 A1.

U.S. Pat. No. 4,685,926 A relates to a prosthetic knee joint having a mechanical lock which can be overridden via a cable pull. A lever mounted in an articulated manner is connected directly to a cable pull and is pivoted when the cable pull is actuated, this resulting in a locking pin moving out of a recess.

DE 28 48 305 A1 relates to a prosthesis joint for the rotatable connection of two prosthesis parts, having a latching body which is mounted in a rotatable manner on one prosthesis part, is fixed to the other prosthesis part and, over its circumference, has latching gaps, into which can be pushed the nose of a locking means which can be guided against the latching body by the pressure of a spring. The locking means serves for locking the joint and latches into the latching gaps. In order to release the joint, the locking means is pulled out, counter to the pressure of the spring, via a cable pull. The locking means, when the nose of the latter is located within the latching gaps of the latching body, can be fixed via an arresting part which can be pushed in between the locking means and the latching body.

DE 10 2012 009 653 A1 relates to a prosthesis joint having an upper part, a lower part and a locking element, wherein the upper part and the lower part are mounted in a pivotable manner on one another. The locking element can be transferred from a release position into a locked position, wherein, in the locked position, the prosthesis joint can be fixed in a predeterminable flexed state and is braced between the upper part and the lower part. A locking lever can transfer the locking element from the locked position into the release position. The locking element is mounted in the upper part, wherein the upper part has an aperture in which the locking element is mounted in a displaceable manner.

DE 20 2008 002 764 U1 relates to an unlocking mechanism for locked knee joints in the fields of orthopedics, in the case of which finger pressure applied to a push rod moves a lever from its starting position into an end position. This results in deflection of movements by 90° and a transmission of ratio 1:2, in which case a horizontal push-rod movement results in the lever moving vertically by double the distance. Actuation gives rise to unlocking counter to a spring in the knee joint, said spring providing for a restoring force into the starting position. The unlocking mechanism is incorporated by molding.

SUMMARY

The problem of the present invention is that of providing an orthopedic joint system which requires the smallest possible amount of installation space and is of inexpensive construction, so that the costs for such an orthopedic joint system can be minimized.

This problem is solved according to the invention by an orthopedic joint system having the features of the main claim and of the alternative independent claim. Advantageous configurations and developments of the invention are disclosed in the dependent claims, the description and the figures.

The orthopedic joint system having an upper part and a lower part, which is mounted on the upper part such that it can be pivoted about a pivot axis, and a catch, which, in a locked position, locks movement of the upper part relative to the lower part about the pivot axis and, in a release position, allows relative movement about the pivot axis, wherein, in the locked position, the catch engages in a form-fitting manner in a locking element and can be shifted into the release position via a pulling element, wherein the pulling element has a first end secured on the upper part or lower part, and, at least in the locked position of the catch, is guided in a curved portion along the outside of the catch, with no engagement therewith, and a second end of the pulling element is provided with an actuating device, makes provision that by actuation of the actuating device the curved portion is shortened and the catch can be brought into the release position. Guiding the curved portion past the catch makes it possible to dispense with a lever arrangement with a two-armed lever, since the pulling element is no longer used to pivot a lever in order to disengage a catch or a pin from a locking element. Rather, the catch is moved into the release position by the shortening of the pulling element in the region of the curved portion. The curved pulling-element portion, which is guided on the outside of the catch or an abutment element fastened or formed on said catch, gives rise to a direct introduction of force, and it is therefore possible to dispense with deflecting levers, a two-armed lever solution and deflecting means for the pulling element. The curved portion is straightened, and the pulling element is in direct contact with the catch, and therefore, without any lever solution or deflecting elements, the shortening of the curved portion when the pulling element is pulled disengages the catch from the locking element and unlocks the orthopedic joint system. The pulling element may be designed in the form of a rope, wire or ribbon and is preferably elastic, but stable in relation to tension, that is to say it lengthens only to an insignificant extent, if at all, when subjected to a tensile force.

The orthopedic joint system can be used as a joint system both in an orthosis and in a prosthesis and can be designed, and configured, in the form of a joint system for a knee joint, ankle joint, hip joint, shoulder joint, elbow joint, wrist joint or finger joint.

The locking element, in which the catch engages in a form-fitting manner, can be formed as a recess in the upper part or in the lower part; as an alternative, it is possible for a protrusion to be formed or arranged on the lower part or the upper part, in which case the catch engages behind the protrusion such that form-fitting locking is present between the catch and locking element. Configuration in the form of a recess facilitates the guidance of the pulling element in the region of the recess, advantageously within the recess.

It is advantageously the case that the first end of the pulling element, rather than being fastened on the catch, is fastened only on the upper part or lower part, the first end advantageously being secured on that component on which the catch is also mounted, that is to say either on the upper part, when the catch is mounted in a rotatable or displaceable manner on the upper part, or conversely on the lower part, the locking element being arranged, formed or fastened on the corresponding other part of the orthopedic joint system.

The pulling element can be guided on a catch nose or on an abutment element, which is arranged on the catch. Guidance of the pulling element on the catch nose has the advantage that the form-fitting element of the catch serves, at the same time, as an abutment for the pulling element, and there is therefore no need for any further component for guiding a pulling element. Providing an abutment element on the catch increases the options of guiding the pulling element such that a user can operate the same straightforwardly, or improved guidance of the pulling element can be achieved, so that the actuating function can be executed reliably and straightforwardly.

The catch can be prestressed elastically in the direction of the locked position, for example by a spring or an elastomeric element, and therefore, following unlocking of the prosthetic knee joint and pivoting of the upper part relative to the lower part from the extended position into a flexed position, after the user has stood up or the knee joint has been extended, locking of the catch in the locking element or with the locking element takes place automatically.

This ensures that, once the extension position has been reached, the orthopedic joint system, e.g. the prosthetic knee joint, orthotic knee joint or some other prosthesis joint or orthosis joint, is locked and the patient enjoys a maximum level of (stance) stability.

The pulling element can be guided between the catch and the locking element, that is to say it can be clamped in for example between the catch and the locking element, and therefore it is positioned within the form-fitting arrangement of the catch and locking element. The pulling element can be guided in a specifically designed guide in the locking element or the catch, for example the locking element, if designed in the form of a recess, can have a groove or a slot formed in it, the pulling element being guided in said groove or slot and being positioned therein in the locked position. The curved portion is then formed in the guide.

The first end of the pulling element can be secured on that component of the prosthetic knee joint which has the locking element, wherein said component also has, at the same time, the pulling-means guide, for example the slot or the groove, in which the pulling element is positioned, and therefore, despite the catch giving rise to the blocking action, direct clamping and pinching of the pulling element is nevertheless avoided.

Also provided is an orthopedic joint system having an upper part and a lower part, which is mounted on the upper part such that it can be pivoted about a pivot axis, wherein the upper part and the lower part have set up between them a hydraulic damper arrangement, which has a piston which is mounted in a rotationally secured manner in a cylinder and has a piston rod, wherein an insert, which can be adjusted via the piston rod and has a variable throttle gap, is arranged in the piston. The additional arrangement of a damper device can furnish the patient with a sitting-down aid or can damp the rotary movement, since the damper absorbs load, and therefore there is no need for the patient to support his full weight on the unaided leg or, via the upper extremities, on walking aids or other objects or, if the joint system is arranged at some other location, there is no need for the patient to absorb the full load which is acting on the joint.

The variable throttle gap makes it possible for the damping rate of the hydraulic damper to be adjusted individually. The adjustment capability via the piston rod facilitates the adjustment procedure on account of the piston rod being easily accessible.

It is possible for the adjustable insert to be mounted displaceably in the direction in which the piston is shifted, in the piston or to be round and mounted in a rotatable manner within the piston, so that, by virtue of the location of the insert within the piston being changed, it is possible to vary the cross section of the throttle gap, the throttle gap being reduced in order to increase damping and being increased in order to reduce damping.

The insert can be mounted in an adjustment ring, which is mounted in a rotationally secured manner in the piston, it therefore being possible for example for channels and/or encircling or partially encircling grooves for forming a throttle gap to be produced straightforwardly in the adjusting ring or the insert and then to be installed definitively in the piston. The piston can comprise the insert and the adjustment ring and can provide for separation between an extension chamber and a flexion chamber.

The adjustment ring and the insert can each respectively contain a channel which is connected in flow terms to the throttle gap, wherein the throttle gap is formed between the adjustment ring and the insert. The channel establishes the respective connection from the flexion chamber to the throttle gap and from the extension chamber to the throttle gap.

In order for the cross section of the throttle gap to be varied, said throttle gap may have a cross section which is variable over the adjustment path of the insert, for example by the depth of a groove which, in the case of a round insert, forms the throttle gap in conjunction with the adjustment ring being increased over the circumference, in which case appropriate rotation can result in a reduced quantity of the hydraulic fluid passing through the throttle gap.

The piston and the cylinder are advantageously of oval design, in order for rotation within the cylinder to be prevented solely by way of the shaping of the piston. The oval shaping allows a narrow construction of the hydraulic damper, while providing, at the same time, for sealing and straightforward production.

It is advantageously the case that both the piston and the cylinder are produced from a plastics material, so that the hydraulic damper can be as lightweight as possible. A variant of the invention provides for either the piston or the cylinder to be formed entirely from a plastics material, so as to achieve, on the one hand, straightforward production and low weight and, on the other hand, a high loading capability provided for by the selection of another material. It is possible for the piston to be produced from a metal, for example steel or aluminum, and to have a piston ring made of plastics material, in particular if the cylinder is produced from a plastics material. This allows the construction of the hydraulic damper to be lightweight. It is also possible for only part of the piston, e.g. the adjustment ring, to consist of a metal, a piston ring made of plastics material being secured in an annular groove on the circumference of said adjustment ring and the insert, which may be produced from plastics material, being inserted in the adjustment ring. Conversely, it is possible for the insert, with the connection to the piston rod, to be formed from a metal and to be mounted in an adjustment ring made of plastics material. If the cylinder is produced from a metal, it is advantageous, albeit not absolutely necessary, for the piston ring likewise to be produced from a metal.

The piston contains at least one check valve, which closes a bypass of the throttle gap, in which case extension of the prosthetic knee joint, with appropriate positioning of the check valve, is always possible in an unimpeded, or virtually unimpeded, manner.

A check valve can also be spring-loaded by a prestressing force, and therefore it is only once a certain pressure within the flexion chamber or extension chamber has been reached that the valve opens and releases the short-circuit line between the extension chamber and the flexion chamber in the form of the bypass of the throttle gap.

BRIEF DESCRIPTION OF THE DRAWINGS

Exemplary embodiments of the invention will be explained in more detail hereinbelow with reference to the accompanying figures, in which.

DETAILED DESCRIPTION

Figure 1:
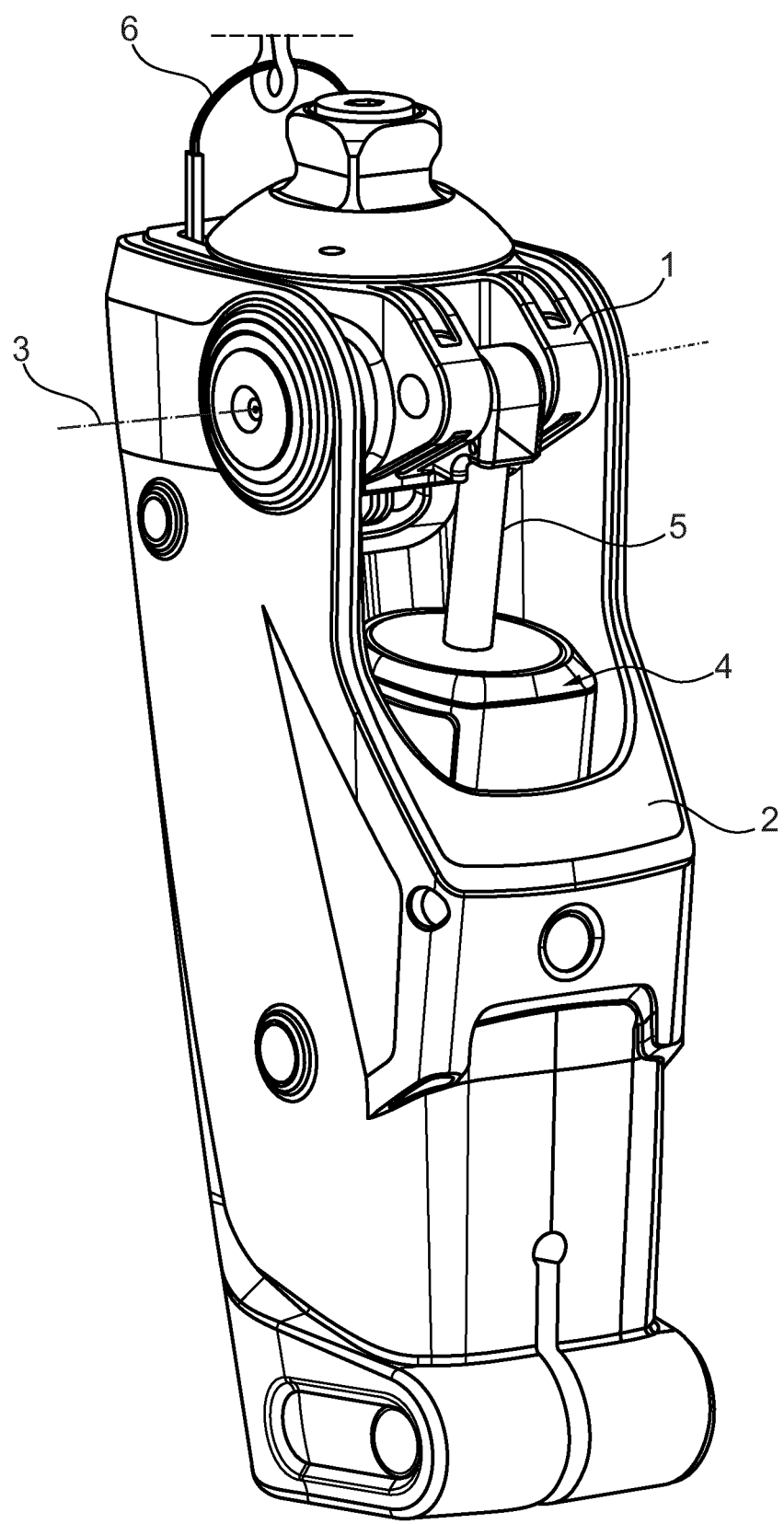
FIG. 1 shows a perspective overall view of the prosthetic knee joint.

FIG. 1 shows a perspective view of a prosthetic knee joint in the form of a lockable knee joint having an upper part 1, which is mounted on a lower part 2 about a pivot axis 3. The prosthetic knee joint is designed in the form of a single-axis knee joint, of which the upper part 1 has a bearing pin for a piston rod 5 of a hydraulic damper 4 behind the pivot axis 3, as seen in the walking direction. The hydraulic damper 4 damps the pivoting movement of the upper part 1 relative to the lower part 2 about the pivot axis from the straight, extended and locked position illustrated into a flexed position, for example when the user is sitting or sitting down. The prosthetic knee joint is locked in a form-fitting manner by a catch (not shown in FIG. 1); the locking means can be released via a pulling element 6.

Figure 2:
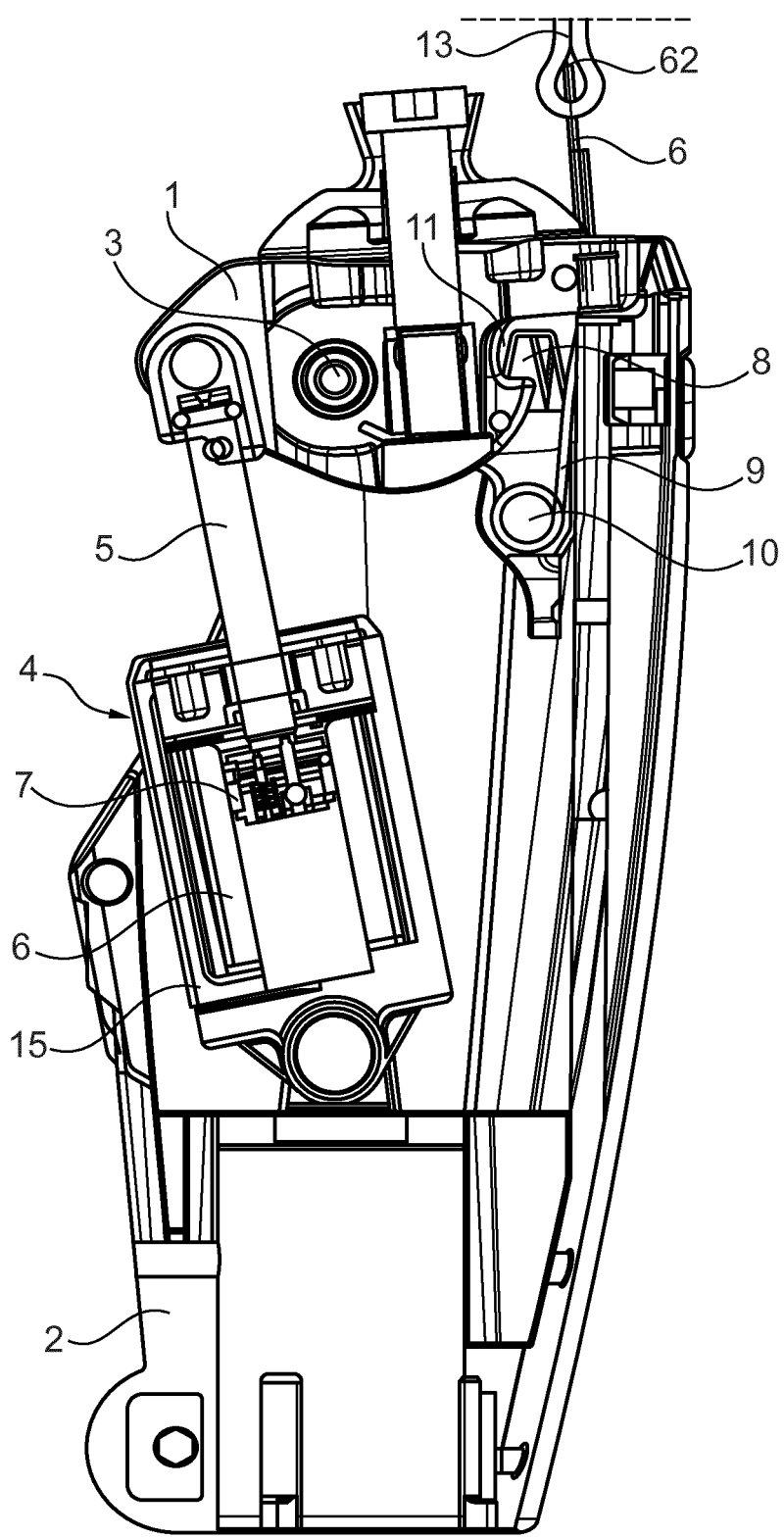
FIG. 2 shows a sectional illustration according to FIG. 1.

FIG. 2 shows a sectional view of the prosthetic knee joint from FIG. 1. The upper part 1 is mounted on the lower part 2 such that it can be pivoted about the pivot axis 3, which is oriented perpendicularly to the drawing plane. The hydraulic damper 4 is mounted pivotably via axes both on the upper part 1 and the lower part 2. The hydraulic damper 4 is connected to the upper part 1 via a piston rod 5; the damper housing 15 is mounted on the lower part 2. The damper housing 15 contains an oval cylinder 6, in which a piston 7, which is coupled to the piston rod 5, is mounted in a longitudinally displaceable manner. The piston 7 separates an extension chamber of the hydraulic cylinder 4 in flow terms from a flexion chamber, an overflow device in the form of a throttle gap, which will be explained in more detail at a later stage in the text, being provided.

Likewise arranged in a pivotable manner on the lower part 2 is a catch 8, which is mounted such that it can be moved about a pivot axis 10. The catch 8 is prestressed in the direction of a locking element 11 via a spring 9. The locking element 11 is designed in the form of a recess, in which the catch 8, which has a form-fitting element in the form of a locking nose, engages in a form-fitting manner. The recess 11 and the locking nose of the catch 8 are of corresponding shaping, and therefore, in the locked state illustrated, pivoting of the upper part 1 relative to the lower part 2 about the pivot axis 3 is prevented.

The catch 8 is assigned a pulling element 6, which is guided along the catch 8 and has a first end (not illustrated) secured on the upper part 1 or the lower part 2. The pulling element 6 is guided, in the locked position illustrated, in a curve along the catch 8 and is provided with a second end 62, which is coupled to an actuating device 13. If the actuating device 13 is pulled upward, or the second end 62 is shifted directly in the proximal direction, the curve shortens, the catch 8 is disengaged from the recess 11 about the pivot axis 10, counter to the spring 9, and a release position is established.

Figure 3A:
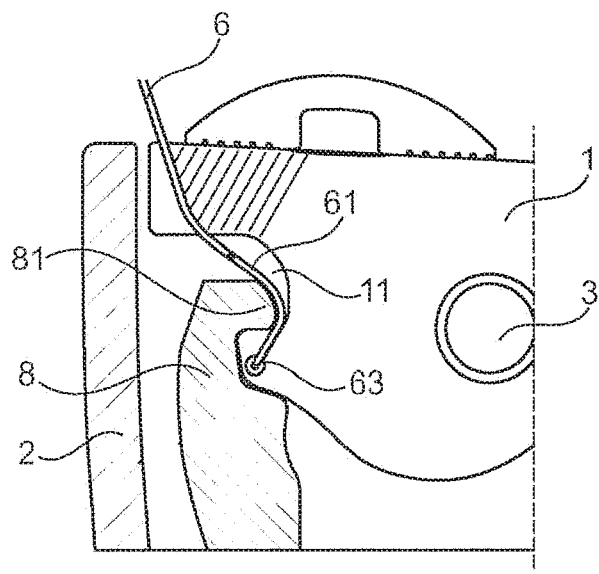
FIG. 3a shows a schematic illustration of the prosthetic knee joint in the locked position.

FIG. 3a shows a schematic illustration of the arrangement of the pulling element 6, of the catch 8 and of the upper part 1 in the locked position. A first end 63 is secured on the upper part 1, and the curved portion 61 of the pulling element 6 is guided on the front end of the locking nose 81 of the catch 8, and therefore, when the pulling element 6 is not actuated, the curved portion 61 butts loosely against the outside of the catch nose 81. Rather than being fastened on the catch 8, the curved portion 61 merely butts against the outside of the same. The catch 8 is mounted on the lower part 2 such that it can be pivoted about the pivot axis 10 (shown in FIG. 2). In the locked position illustrated, rotation of the upper part 1 in relation to the lower part 2 about the pivot axis 3 is prevented.

Figure 3B:
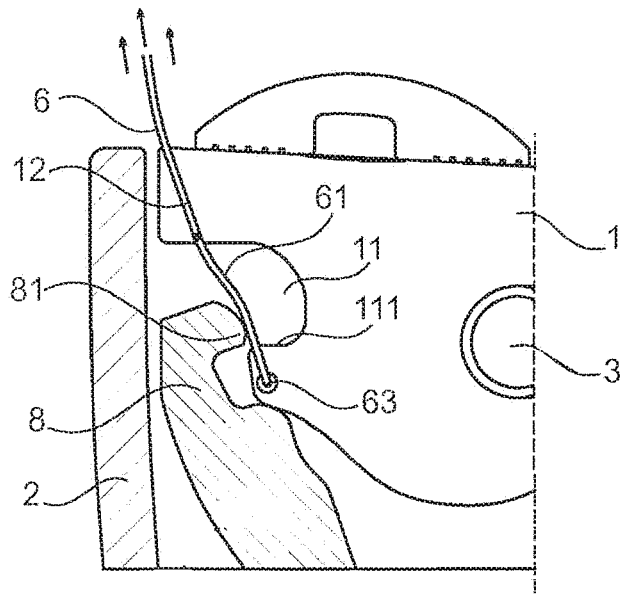
FIG. 3b shows an arrangement according to FIG. 3a in the release position.

FIG. 3b shows the mode of operation of the unlocking. The pulling element 6 is pulled upward in the arrow direction, in which case the pulling element 6 straightens and has the tendency to straighten the curved portion 61. The pulling element 6 thus pushes on the front portion of the catch nose 81 from the outside, and therefore the catch 8 is disengaged from the recess 11 within the upper part 1 about the pivot axis 10 (shown in FIG. 2), counter to the prestressing force of the spring (not illustrated). The form-fitting locking by the catch nose 81 is overridden, the catch nose 81 is moved away from the corresponding abutment surface 111 in the recess 11 and the pulling element 6 is moved into a straightened position, starting from the point at which the first end 63 of the pulling element is secured. A pulling-element guide 12 in the form of a slot and of a guide slope is formed within the upper part 1, in which case the pulling element 6 cannot move out of the recess 11. It is also possible for the guide 12 of the pulling element 6 to be designed in the form of a channel with three abutment sides or of a closed lead-through in the form of a bore.

Figure 3C:
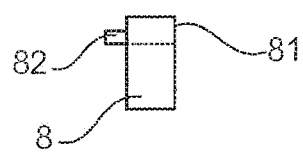
FIG. 3c shows a plan view of a catch.

FIG. 3c shows a schematic illustration of a catch in plan view. The pivoting capability about the pivot axis 10 (shown in FIG. 2) is indicated, in addition to the form-fitting locking means being configured by a locking nose 81, it is possible for an abutment element 82 to be fitted, or provided, laterally alongside the locking nose 81, in order to provide the pulling element 6 with guidance there.

FIG. 3c shows a schematic illustration of a catch in plan view. The pivoting capability about the pivot axis is indicated, in addition to the form-fitting locking means being configured by a locking nose 81, it is possible for an abutment element 82 to be fitted, or provided, laterally alongside the locking nose 81, in order to provide the pulling element 6 with guidance there.

Figure 4:
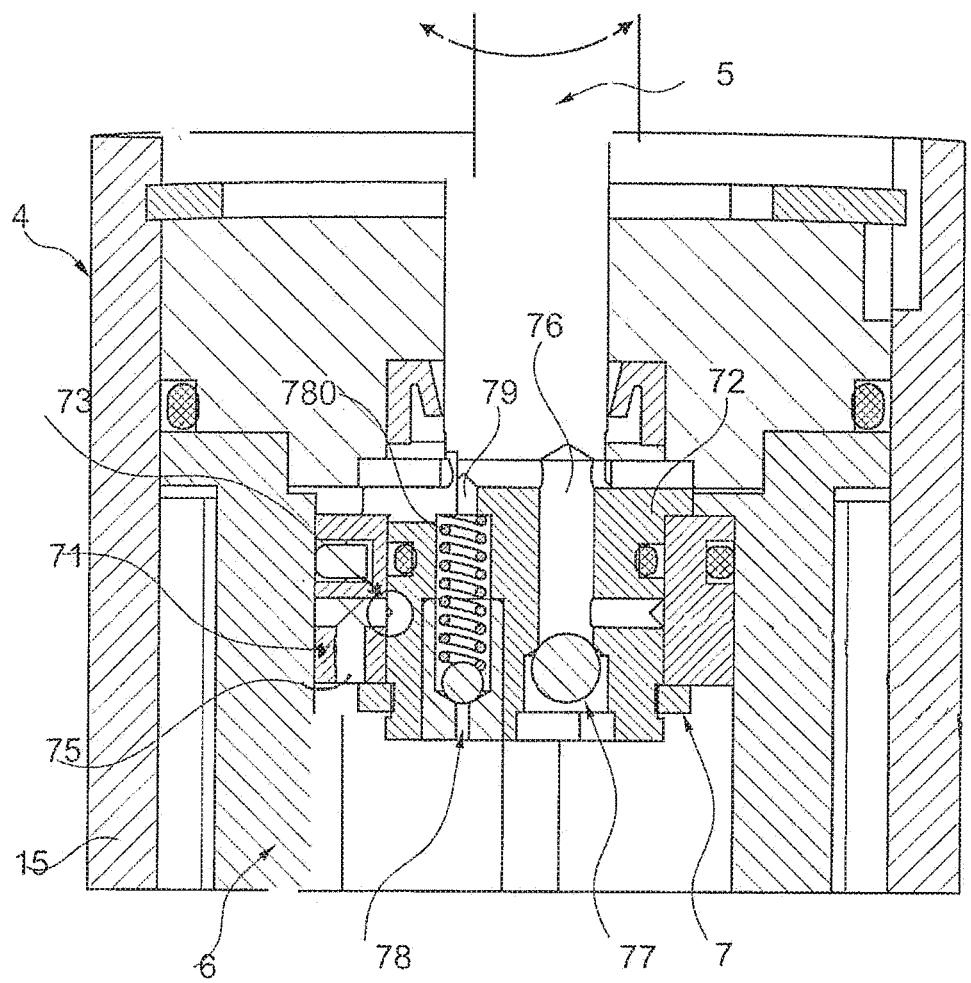
FIG. 4 shows a detail-view illustration, as seen in longitudinal section, of the hydraulic damper.

FIG. 4 shows a sectional illustration through part of the hydraulic damper 4. The hydraulic damper 4 provides, in its housing 15, an oval cylinder 6, in which is arranged a piston 7, which separates an extension chamber from a flexion chamber. The piston 7 is connected to the upper part 1 of the prosthetic knee joint (not illustrated) via a piston rod 5. The piston 7 comprises an outwardly oval adjustment ring 71, which is mounted within the cylinder 6 in a rotationally secured manner and such that it can be displaced along the longitudinal extent of the piston rod 5. A round insert 72 is arranged in a rotatable manner centrally within the adjustment ring 71, wherein the insert 72 is coupled in a rotationally fixed manner to the piston rod 5. The ability of the piston rod 5 to rotate is indicated by the double arrow. If, then, the piston rod is subjected to pressure as a result of the prosthetic knee joint being flexed, hydraulic fluid flows from the lower flexion chamber, through a channel 75, into the adjustment ring 71 and to a throttle gap 73, which is formed between the adjustment ring 71 and the insert 72. The throttle gap 73 is formed by an encircling or partially encircling groove within the insert 72, wherein the damping action of the hydraulic damper is defined by the smallest cross section, which in the exemplary embodiment illustrated is located at the encircled throttle gap 73. The insert 72 has formed around its circumference a groove which becomes deeper in the circumferential direction and is in flow connection with a second channel 76, and therefore, when the prosthetic knee joint 1 is flexed, the hydraulic fluid flows into the flexion chamber from the extension chamber, through the channel 75, through the throttle gap 73 and through the second channel 76. The channel 76 is in direct flow connection with the flexion chamber.

The channel 76 contains a check valve 77, which prevents direct through-passage from the extension chamber to the flexion chamber when the prosthetic knee joint is flexed. In the case of movement being reversed, that is to say in the case of the lower part being extended relative to the upper part 1, the hydraulic fluid flows from the flexion chamber, through the channel 76, in the direction of the check valve 77, displaces the arresting ball from the valve seat and allows the fluid to flow back from the flexion chamber into the extension chamber in a virtually unimpeded manner. It is thus possible to achieve a defined resistance to flexion by varying the cross section of the throttle gap 73, without significantly impeding the standing-up action.

In addition, the insert 72 contains a further channel 79, which is closed by a check valve 78, which is pressed into the valve seat via a spring 780. The second check valve 78 acts counter to the first check valve 77 and serves as an overload valve, which prevents possible mechanical damage on account of excessive pressures or, in the case of incorrect adjustment of the cross section of the throttle gap, also allows damage and flexion of the prosthetic knee joint in the case of emergency.

Instead of the rotary adjustment capability of the cross section of the throttle gap 73 illustrated, it is possible to achieve axial displaceability of the insert by rotation of the piston rod 5 relative to the rotationally fixed piston 7, so as to allow for variation of the cross section of the throttle gap by appropriate shifting relative to the adjustment ring 71.

Even without the prosthetic knee joint, the configuration of the hydraulic damper 4 in the illustrated form designed with the rotationally fixed, but axially displaceable piston 7 constitutes an independent solution to the problem as a straightforward hydraulic damping means with easy adjustability and inexpensive production on account of plastics materials being used.

Figure 5:
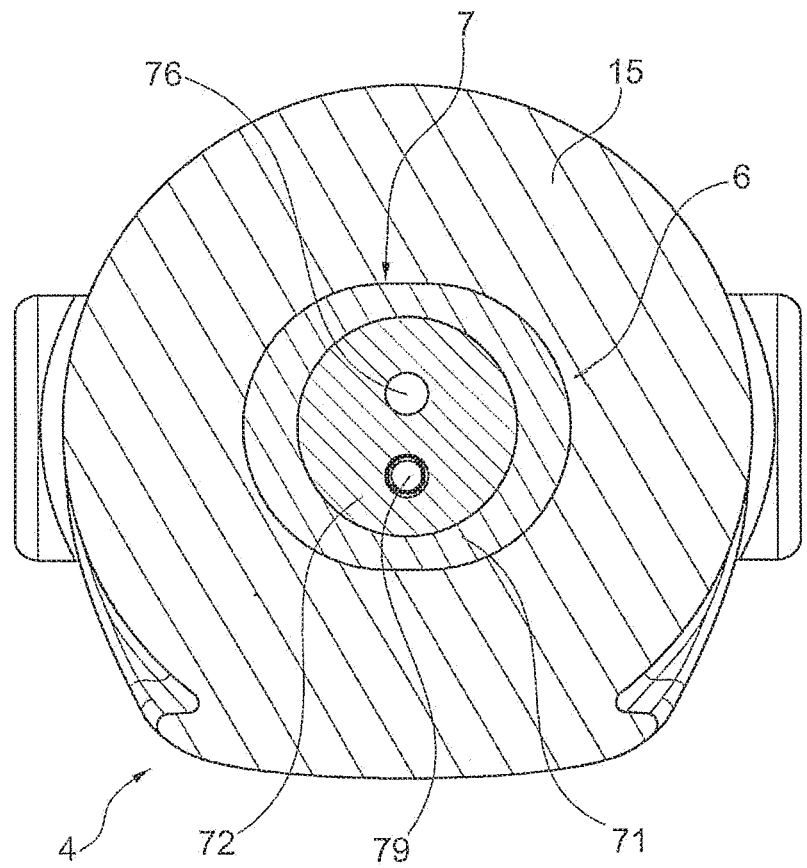
FIG. 5 shows a cross-sectional view of the hydraulic damper.

FIG. 5 shows a sectional illustration through the hydraulic damper 4 taken level with the piston 7 and in a direction perpendicular to the direction in which the latter is shifted. The cylinder 6 is formed in the housing 15 and has an oval contour. The cylinder 6 contains the piston 7, which likewise has a corresponding, oval outer contour. The piston 7 has an outer adjustment ring 71 as a constituent part of the piston, which forms the oval and thus rotationally secured outer contour and has a round inner recess, in which the insert 72 is mounted in a rotatable manner. The two channels 76, 79 can be seen in the insert 72, said channels providing for a connection between the extension chamber and the flexion chamber. The upper channel 76 is connected via a radial bore to the groove which forms the throttle gap 73, and therefore, in the case of an open throttle gap, there is a flow connection from the flexion chamber, through the channel 75 in FIG. 4, the throttle gap 73 and the radial bore and the channel 76, to the extension chamber. The lower channel 79 serves as a flow connection and bypass in the event of overloading, and therefore, in the case of too high a pressure within the flexion chamber, the safety valve designed in the form of a check valve opens and thus allows the joint system to flex. The oval piston 7 has mounted in it the insert 72, which can be rotated in the adjustment ring 71 and, by virtue of the piston rod 5 being rotated about its longitudinal axis, can be adjusted in its position or orientation in the adjustment ring 71, it therefore being possible for the flow resistance to be varied by virtue of the cross section of the throttle gap being varied.

The invention claimed is:

1. An orthopedic joint system, comprising:
   an upper part;
   a lower part, which is mounted on the upper part such that the lower part can be pivoted about a pivot axis;
   a locking element;
   a pulling element having a first end secured on the upper part or lower part and a second end provided with an actuating device;
   a catch, which, in a locked position, locks movement of the upper part relative to the lower part about the pivot axis and, in a release position, allows relative movement about the pivot axis, wherein, in the locked position, the catch engages in a form-fitting manner in the locking element and can be shifted into the release position via the pulling element, the catch including a curved portion along an outer surface of the catch;
   wherein by actuation of the actuating device an amount of the pulling element in contact with the curved portion is reduced and the catch is brought into the release position.

2. The orthopedic joint system as claimed in claim 1, wherein the pulling element comprises a rope, wire or ribbon.

3. The orthopedic joint system as claimed in claim 1, wherein the locking element comprises a recess in, or a protrusion on, the lower part or the upper part.

4. The orthopedic joint system as claimed in claim 1, wherein the first end of the pulling element is detached from the catch.

5. The orthopedic joint system as claimed in claim 1, wherein the pulling element is guided on a nose of the catch or an abutment element, which is arranged on the catch.

6. The orthopedic joint system as claimed in claim 1, wherein the catch is mounted in a pivotable or longitudinally displaceable manner in the upper part or lower part.

7. The orthopedic joint system as claimed in claim 1, wherein the catch is prestressed elastically in a direction of the locked position.

8. The orthopedic joint system as claimed in claim 1, wherein the pulling element is guided between the catch and the locking element.

9. The orthopedic joint system as claimed in claim 1, wherein the first end of the pulling element is secured on a component of the orthopedic joint system which has the locking element, and the component has a pulling guide.

10. An orthopedic joint system, comprising:
an upper part;
a lower part, which is mounted on the upper part such that the lower part can be pivoted about a pivot axis;
a hydraulic damper device arranged between the upper part and the lower part, the hydraulic damper device having a cylinder, a piston, and a piston rod, the piston having a fixed rotated position within the cylinder;
an insert arranged in the piston, the insert being adjustable by rotation of the piston rod relative to the piston, the insert having a variable throttle gap.

11. The orthopedic joint system as claimed in claim 10, wherein the insert is displaceably mounted in the piston in a direction in which the piston is movable within the cylinder, or is designed to be round and is mounted in a rotatable manner in the piston.

12. The orthopedic joint system as claimed in claim 10, wherein the insert is mounted in an adjustment ring, which is mounted in a rotationally secured manner in the piston.

13. The orthopedic joint system as claimed in claim 12, wherein the adjustment ring and the insert each respectively contain a channel which is connected in flow communication with the throttle gap, the throttle gap being formed between the adjustment ring and insert.

14. The orthopedic joint system as claimed in claim 10, wherein the throttle gap has a cross section which is variable over an adjustment path of the insert.

15. The orthopedic joint system as claimed in claim 10, wherein the piston and cylinder have an oval cross-sectional shape.

16. The orthopedic joint system as claimed in claim 10, wherein the piston contains at least one check valve, which closes a bypass of the throttle gap.

17. The orthopedic joint system as claimed in claim 16, wherein the at least one check valve is spring-loaded.

18. The orthopedic joint system as claimed in claim 10, wherein at least one of the piston and the cylinder is produced, at least in part, from a plastics material.

19. The orthopedic joint system as claimed in claim 10, wherein the joint system is designed in the form of a lockable knee joint.

20. An orthopedic joint system, comprising:
an upper part;
a lower part pivotally mounted to the upper part about a pivot axis;
a catch having a locked position in which movement of the upper part relative to the lower part about the pivot axis is locked, a release position in which the upper part is movable relative to the lower part about the pivot axis, and a curved portion along an outer surface of the catch;
a locking element configured to receive the catch when in the locked position;
a pulling element operable to move the catch into the release position, the pulling element comprising:
a first end secured on the upper part or the lower part and being guided in the curved portion along an outside of the catch;
a second end provided with an actuating device, wherein operating the actuating device reduces an amount of the pulling element in contact with the curved portion and moves the catch into the release position.

* * * * *